(12) United States Patent
Rothstein

(10) Patent No.: US 10,646,333 B2
(45) Date of Patent: May 12, 2020

(54) TWO-PIECE VALVE PROSTHESIS WITH ANCHOR STENT AND VALVE COMPONENT

(71) Applicant: Medtronic, Inc., Minneapolis, MN (US)

(72) Inventor: Paul Rothstein, Elk River, MN (US)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 14/062,457

(22) Filed: Oct. 24, 2013

(65) Prior Publication Data

US 2015/0119974 A1    Apr. 30, 2015

(51) Int. Cl.
  *A61F 2/24* (2006.01)
  *A61F 2/852* (2013.01)
  *A61F 2/82* (2013.01)

(52) U.S. Cl.
  CPC ............ *A61F 2/2418* (2013.01); *A61F 2/852* (2013.01); *A61F 2002/826* (2013.01); *A61F 2220/0008* (2013.01); *A61F 2220/0025* (2013.01); *A61F 2250/006* (2013.01)

(58) Field of Classification Search
  CPC ........ A61F 2/2409; A61F 2/24; A61F 2/2418; A61F 2002/828; A61F 2250/0039; A61F 2250/0007; A61F 2/2427
  See application file for complete search history.

(56) References Cited

U.S. PATENT DOCUMENTS

| | | |
|---|---|---|
| 3,574,865 A | 4/1971 | Hamaker |
| 3,671,979 A | 6/1972 | Moulopoulos |
| 3,997,923 A | 12/1976 | Possis |
| 4,056,854 A | 11/1977 | Boretos et al. |
| RE31,040 E | 9/1982 | Possis |
| 4,506,394 A | 3/1985 | Bedard |
| 4,705,516 A | 11/1987 | Barone et al. |
| 4,790,843 A | 12/1988 | Carpentier et al. |

(Continued)

FOREIGN PATENT DOCUMENTS

| | | |
|---|---|---|
| FR | 2906454 | 4/2008 |
| WO | WO2000/047139 | 8/2000 |

(Continued)

OTHER PUBLICATIONS

Bonhoeffer P., et al., "Percutaneous Insertion of the Pulmonary Valve", Pediatric Cardiology, 2002; 39:1664-1669.

(Continued)

*Primary Examiner* — Brian E Pellegrino
(74) *Attorney, Agent, or Firm* — Medler Ferro Woodhouse & Mills PLLC

(57) ABSTRACT

A modular valve prosthesis includes an anchor stent and a valve component. The anchor stent includes a self-expanding tubular frame member configured to be deployed in the aorta and a proximal arm component extending from a proximal end of the tubular frame member and configured to be deployed in the sinuses of the aortic valve. The anchor stent further includes attachment members extending from an internal surface of the tubular frame member. The valve component includes a valve frame configured to be deployed within the tubular frame member of the anchor stent such that the valve frame engages with the attachment members of the tubular frame member and a prosthetic valve coupled to the valve frame.

10 Claims, 12 Drawing Sheets

(56) References Cited

U.S. PATENT DOCUMENTS

| | | | |
|---|---|---|---|
| 4,994,077 A | 2/1991 | Dobben | |
| 5,032,128 A | 7/1991 | Alonso | |
| 5,332,402 A | 7/1994 | Teitelbaum | |
| 5,370,685 A | 12/1994 | Stevens et al. | |
| 5,397,351 A | 3/1995 | Pavcnik et al. | |
| 5,554,185 A | 9/1996 | Block et al. | |
| 5,716,370 A | 2/1998 | Williamson, IV et al. | |
| 5,855,601 A | 1/1999 | Bessler et al. | |
| 5,984,959 A | 11/1999 | Robertson et al. | |
| 6,074,418 A | 6/2000 | Buchanan et al. | |
| 6,106,550 A | 8/2000 | Magovern | |
| 6,168,614 B1 | 1/2001 | Andersen et al. | |
| 6,176,877 B1 | 1/2001 | Buchanan et al. | |
| 6,217,611 B1 | 4/2001 | Klostermeyer | |
| 6,419,696 B1 | 7/2002 | Ortiz et al. | |
| 6,425,916 B1 | 7/2002 | Garrison et al. | |
| 6,468,305 B1 | 10/2002 | Otte | |
| 6,569,196 B1 | 5/2003 | Vesely | |
| 6,730,121 B2 | 5/2004 | Ortiz et al. | |
| 6,764,508 B1 | 7/2004 | Roehe et al. | |
| 6,786,925 B1 | 9/2004 | Schoon et al. | |
| 6,790,229 B1 | 9/2004 | Berreklouw | |
| 6,846,325 B2 | 1/2005 | Liddicoat | |
| 6,893,459 B1 | 5/2005 | Macoviak | |
| 6,908,481 B2 | 6/2005 | Cribier | |
| 6,939,365 B1 | 9/2005 | Fogarty et al. | |
| 6,964,684 B2 | 11/2005 | Ortiz et al. | |
| 7,097,659 B2 | 8/2006 | Woolfson et al. | |
| 7,147,663 B1 | 12/2006 | Berg et al. | |
| 7,172,625 B2 | 2/2007 | Shu et al. | |
| 7,186,265 B2 | 3/2007 | Sharkawy et al. | |
| 7,291,168 B2 | 11/2007 | Macoviak et al. | |
| 7,300,463 B2 | 11/2007 | Liddicoat | |
| 7,311,730 B2 | 12/2007 | Gabbay | |
| 7,381,220 B2 | 6/2008 | Macoviak et al. | |
| 7,503,930 B2 | 3/2009 | Sharkawy et al. | |
| 7,513,909 B2 | 4/2009 | Lane et al. | |
| 7,527,646 B2 | 5/2009 | Randert et al. | |
| 7,578,843 B2 | 8/2009 | Shu | |
| 7,597,711 B2 | 10/2009 | Drews et al. | |
| 7,611,535 B2 | 11/2009 | Woolfson et al. | |
| 7,648,528 B2 | 1/2010 | Styre | |
| 7,691,144 B2 | 4/2010 | Chang et al. | |
| 7,708,775 B2 | 5/2010 | Rowe et al. | |
| 7,717,955 B2 | 5/2010 | Lane et al. | |
| 7,722,667 B1 | 5/2010 | Buchanan | |
| 7,758,640 B2 | 7/2010 | Vesely | |
| 7,771,469 B2 | 8/2010 | Liddicoat | |
| 7,871,436 B2 | 1/2011 | Ryan et al. | |
| 7,887,583 B2 | 2/2011 | Macoviak | |
| 7,951,197 B2 | 5/2011 | Lane et al. | |
| 7,959,674 B2 | 6/2011 | Shu et al. | |
| 7,981,153 B2 | 7/2011 | Fogarty et al. | |
| 8,025,695 B2 | 9/2011 | Fogarty et al. | |
| 8,083,793 B2 | 12/2011 | Lane et al. | |
| 8,105,377 B2 | 1/2012 | Liddicoat | |
| 8,163,013 B2 | 4/2012 | Machold et al. | |
| 8,187,207 B2 | 5/2012 | Machold et al. | |
| 8,287,591 B2 | 10/2012 | Keidar et al. | |
| 9,289,282 B2* | 3/2016 | Olson | A61F 2/07 |
| 2002/0032481 A1* | 3/2002 | Gabbay | A61F 2/2418 |
| | | | 623/2.11 |
| 2004/0034411 A1 | 2/2004 | Quijano et al. | |
| 2005/0137686 A1 | 6/2005 | Salahieh et al. | |
| 2006/0178726 A1* | 8/2006 | Douglas | A61F 2/07 |
| | | | 623/1.16 |
| 2006/0287717 A1* | 12/2006 | Rowe et al. | 623/2.11 |
| 2008/0208327 A1 | 8/2008 | Rowe | |
| 2009/0240320 A1* | 9/2009 | Tuval et al. | 623/1.24 |
| 2010/0076548 A1 | 3/2010 | Konno | |
| 2010/0161036 A1 | 6/2010 | Pintor et al. | |
| 2010/0179649 A1 | 7/2010 | Richter et al. | |
| 2010/0249894 A1* | 9/2010 | Oba | A61F 2/2418 |
| | | | 623/2.18 |
| 2010/0249915 A1 | 9/2010 | Zhang | |
| 2010/0262231 A1 | 10/2010 | Tuval et al. | |
| 2010/0312333 A1 | 12/2010 | Navia et al. | |
| 2011/0137397 A1 | 6/2011 | Chau et al. | |
| 2011/0172765 A1 | 7/2011 | Nguyen et al. | |
| 2011/0218619 A1* | 9/2011 | Benichou | A61F 2/2412 |
| | | | 623/2.11 |
| 2012/0041550 A1* | 2/2012 | Salahieh | A61F 2/2418 |
| | | | 623/2.36 |
| 2013/0245753 A1* | 9/2013 | Alkhatib | A61F 2/2418 |
| | | | 623/2.18 |
| 2014/0277573 A1* | 9/2014 | Gill | A61F 2/90 |
| | | | 623/23.68 |
| 2014/0316513 A1* | 10/2014 | Tang | 623/1.16 |
| 2014/0324164 A1* | 10/2014 | Gross | A61F 2/2442 |
| | | | 623/2.37 |

FOREIGN PATENT DOCUMENTS

| | | |
|---|---|---|
| WO | WO2007/081820 | 7/2007 |
| WO | WO2007/130537 | 11/2007 |
| WO | WO2007/149933 | 12/2007 |
| WO | WO2008/101193 | 8/2008 |
| WO | 2013/072496 A1 | 5/2013 |
| WO | 2013/120181 A1 | 8/2013 |

OTHER PUBLICATIONS

Anderson H R, et al., "Transluminal Implantation of Artificial Heart Valves", EUR Heart J., 1992; 13:704-708.

Anderson, H. R., et al., "Transluminal Catheter Implantation of New Expandable Artificial Cardiac Valve (the stent-valve) in the Aorta and the Beating Heart of Closed Chest Pigs", EUR Heart J.[Abstract], 1990;11 (Suppl):224a.

Hilbert S. L., "Evaluation of Explanted Polyurethane Tri Leaflet Cardiac Valve Prosthesis", J Thorac Cardiovascular Surgery, 1989; 94:419-29.

Block P C, "Clinical and Hemodynamic Follow-Up After Percutaneous Aortic Valvuloplasty in the Elderly", The American Journal of Cardiology, vol. 62, Oct. 1, 1998.

Boudjemline, Y., "Steps Toward Percutaneous Aortic Valve Replacement", Circulation, 2002; 105:775-558.

Bonhoeffer, P., "Transcatheter Implantation of a Bovine Valve in Pulmonary Position, a Lamb Study", Circulation, 2000: 102:813-816.

Boudjemline, Y., "Percutaneous Implantation of a Valve in the Descending Aorta in Lambs", EUR Heart J, 2002; 23:1045-1049.

Kulkinski, D., "Future Horizons in Surgical Aortic Valve Replacement: Lessons Learned During the Early Stages of Developing a Transluminal Implantation Technique", ASAIO J, 2004; 50:364-68.

PCT/US2014/058913, PCT International Search Report and the Written Opinion, dated Dec. 23, 2014.

\* cited by examiner

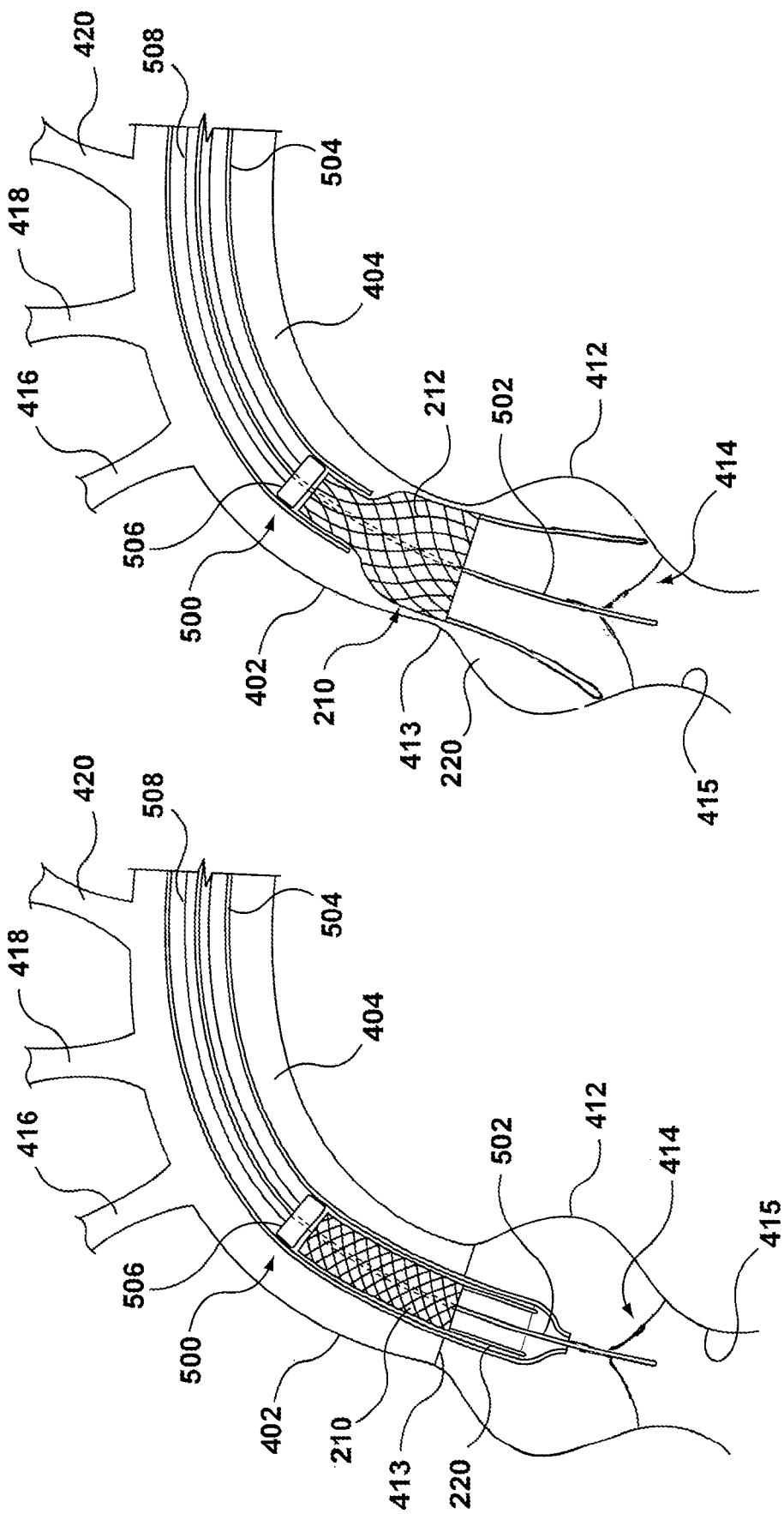

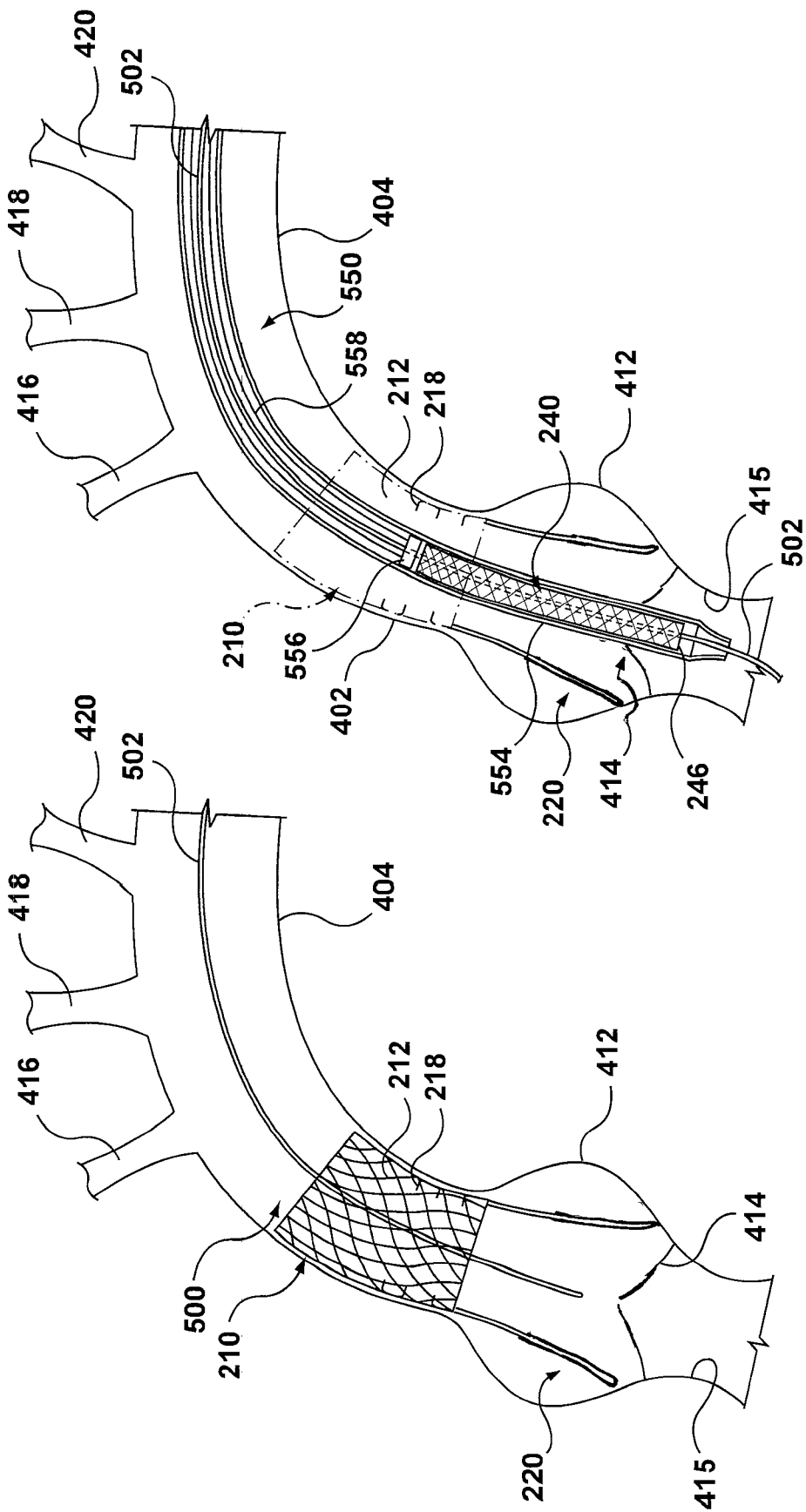

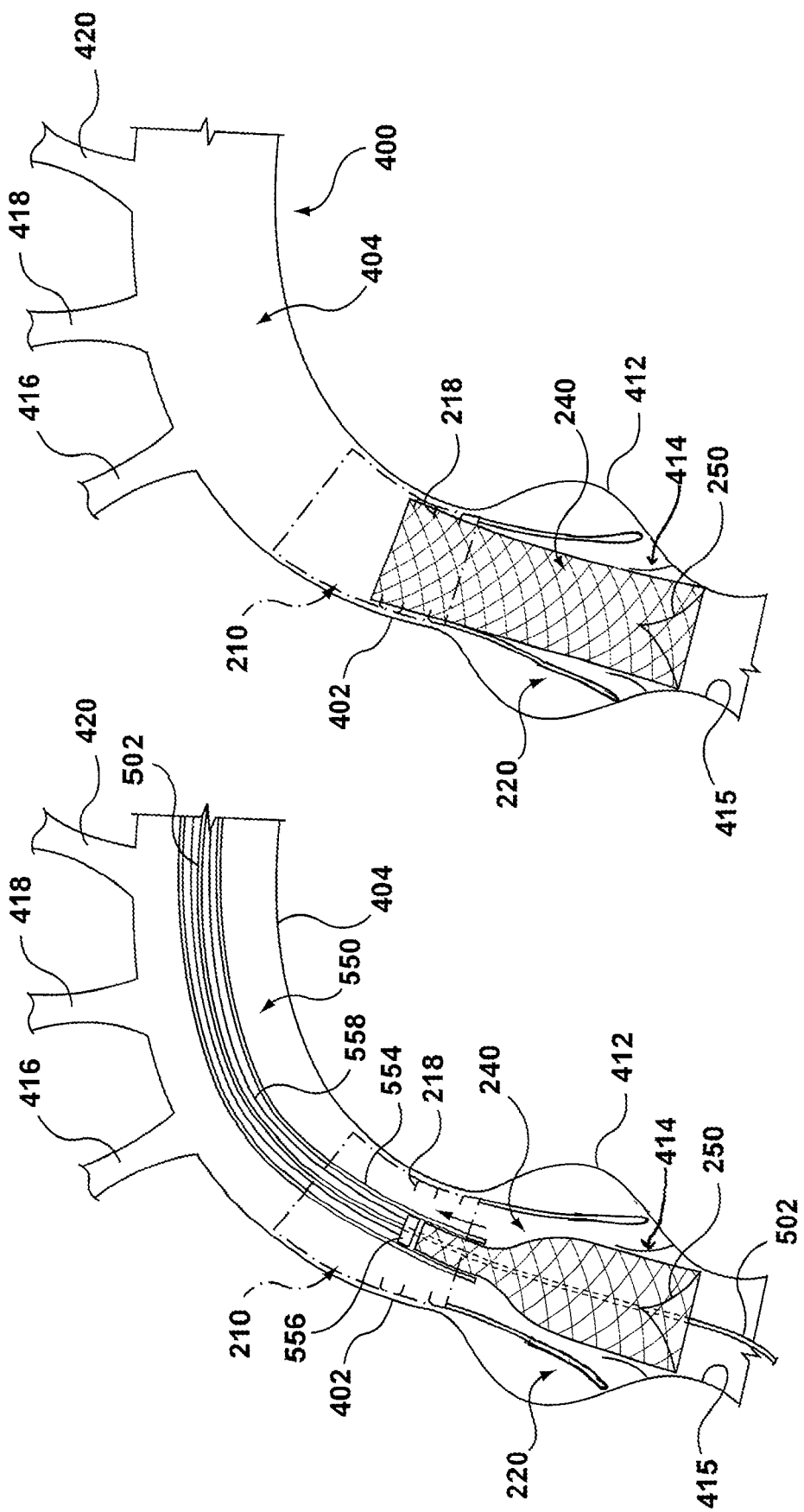

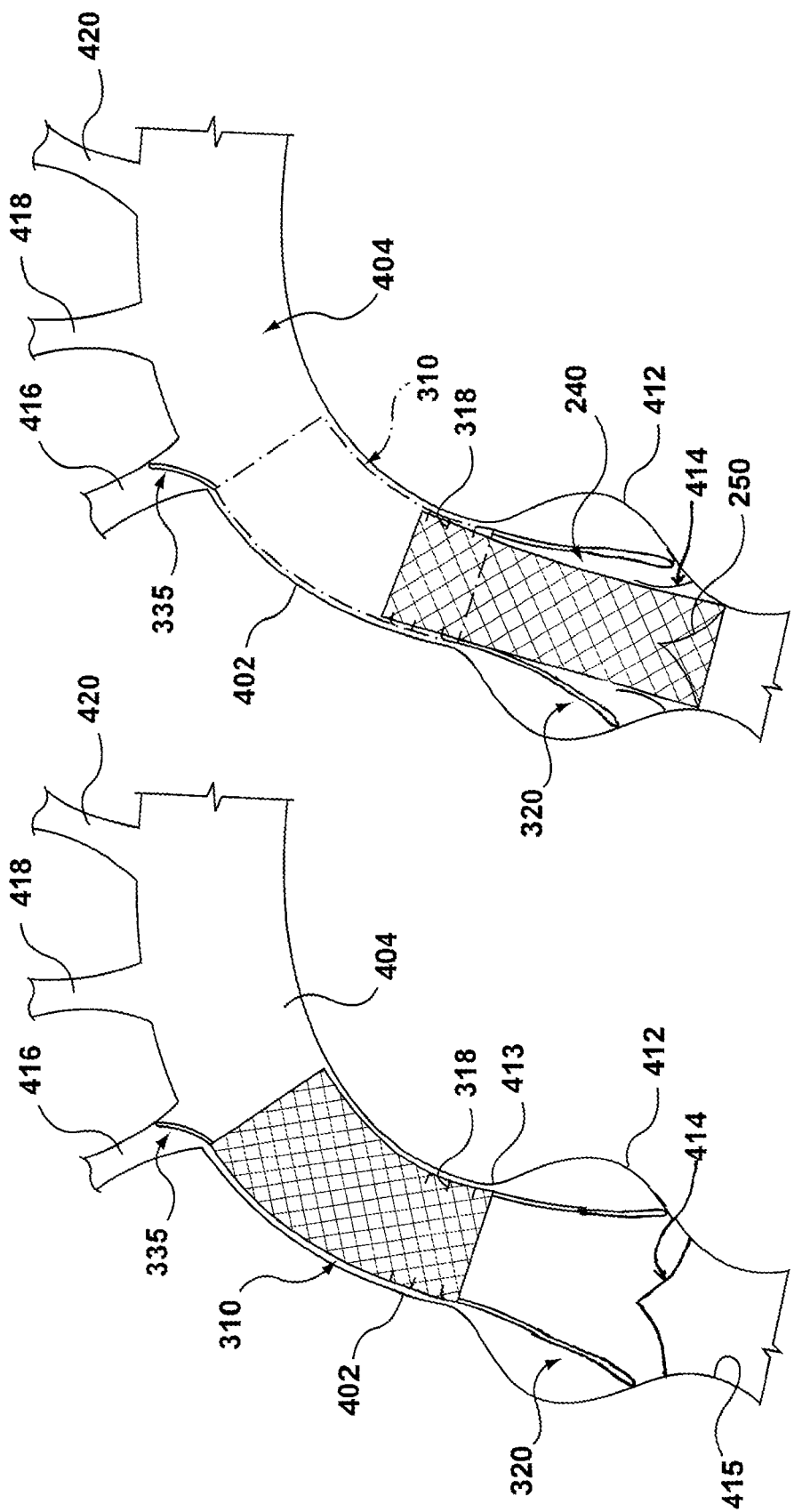

TWO-PIECE VALVE PROSTHESIS WITH ANCHOR STENT AND VALVE COMPONENT

FIELD OF THE INVENTION

Embodiments hereof relate to prosthetic heart, valves and methods for intraluminally deploying, prosthetic heart valves, and in particular, to a modular prosthetic heart valve including an anchor stent and methods of intraluminally deploying the anchor stent and the prosthetic heart valve.

BACKGROUND OF THE INVENTION

Heart valves, such as the mitral, tricuspid, aortic, and pulmonary valves, are sometimes damaged by disease or by aging, resulting in problems with the proper functioning of the valve. Heart valve problems generally take one of two forms: stenosis in which a valve does not open completely or the opening is too small, resulting in restricted blood flow; or insufficiency in which blood leaks backward across a valve when it should be closed.

Heart valve replacement has become a routine surgical procedure for patients suffering from valve regurgitation or stenotic calcification of the leaflets. Conventionally, the vast majority of valve replacements entail full stenotomy in placing the patient on cardiopulmonary bypass. Traditional open surgery inflicts significant patient trauma and discomfort, requires extensive recuperation times, and may result in life-threatening complications.

To address these concerns, efforts have been made to perform cardiac valve replacements using minimally-invasive techniques. In these methods, laparoscopic instruments are employed to make small openings through the patient's ribs to provide access to the heart. While considerable effort has been devoted to such techniques, widespread acceptance has been limited by the clinician's ability to access only certain regions of the heart using laparoscopic instruments.

Still other efforts have been focused upon percutaneous transcatheter (or transluminal) delivery of replacement cardiac valves to solve the problems presented by traditional open surgery and minimally-invasive surgical methods. In such methods, a valve prosthesis is compacted for delivery in a catheter and then advanced, for example through an opening in the femoral artery and through the descending aorta to the heart, where the prosthesis is then deployed in the valve annulus (e.g., the aortic valve annulus).

Various types and configurations of prosthetic heart valves are used in percutaneous valve procedures to replace diseased natural human heart valves. The actual shape and configuration of any particular prosthetic heart valve is dependent to some extent upon the valve being replaced (i.e., mitral valve, tricuspid valve, aortic valve, or pulmonary valve). In general, prosthetic heart valve designs attempt to replicate the function of the valve being replaced and thus will include valve leaflet-like structures used with either bioprostheses or mechanical heart valve prostheses. If bioprostheses are selected, the replacement valves may include a valved vein segment or pericardial manufactured tissue valve that is mounted in some manner within an expandable stent frame to make a valved stent. In order to prepare such a valve for percutaneous implantation, one type of valved stent can be initially provided in an expanded or uncrimped condition, then crimped or compressed around a balloon portion of a catheter until it is close to the diameter of the catheter. In other percutaneous implantation systems, the stent frame of the valved stent can be made of a self-expanding material. With these systems, the valved stent is crimped down to a desired size and held in that compressed state within a sheath, for example. Retracting the sheath from this valved stent allows the stent to expand to a larger diameter, such as when the valved stent is in a desired position within a patient.

With conventional stented valve designs, the stent framework holds the stented valve in place by applying a radial force against the interior of the wall wherein the stent framework is placed. For example, with a stented valve used to replace an aortic valve, the stent framework may support the valve in place by applying a radial force against the annulus, the aortic sinuses, and/or the ascending aorta. With such a stented valve design, the stent framework must be capable of providing sufficient radial force to hold the stented valve in place and must also include the valve prosthesis within the stent framework. Such a device may not be able to be crimped to a desired small diameter to navigate some tortuous or diseased vessels. Further, it may be difficult to adjust the location of such a device during delivery to the desired location. Still further, the operation of the native valve leaflets is interrupted during the delivery of such a device such that it would be desirable to reduce the amount of time the native valve leaflet operation is interrupted.

BRIEF SUMMARY OF THE INVENTION

Embodiments hereof are related to a modular valve prosthesis including an anchor stent and a valve component. The anchor stent includes a self-expanding tubular frame member configured to be deployed in the aorta and a proximal arm component extending from a proximal end of the tubular frame member and configured to be deployed in the sinuses of the aortic valve. The anchor stent further includes attachment members extending from an internal surface of the tubular frame member. The valve component includes a valve frame configured to be deployed within the tubular frame member of the anchor stent such that the valve frame engages with the attachment members of the tubular frame member and a prosthetic valve coupled to the valve frame. In an embodiment the anchor stent may also include a distal arm component extending from a distal end of the tubular frame member configured to be deployed in the brachiocephalic artery. The attachment members of the anchor stent may be barbs, hooks, loops, or any other mechanism for coupling to the valve frame to the anchor stent.

Embodiments hereof are also directed to a method of implanting a modular prosthetic valve at a location of a native aortic valve. In an embodiment, an anchor stent is advanced in a radially compressed configuration into the aorta. The anchor stent includes a tubular frame member, a proximal arm component extending from a first end of the tubular frame member, and a plurality of attachment members extending inwardly from an inner surface of the tubular frame member. The anchor stent is then deployed in the ascending aorta such that the tubular frame member expands from the radially compressed configuration to a radially expanded configuration engaging an inner wall surface the aorta and the proximal arm component expands from the radially compressed configuration to the radially expanded configuration engaging an inner wall surface of the sinuses of the aortic valve. A valve component is then separately advanced in a radially compressed configuration into the aorta. The valve component includes a valve frame and a prosthetic valve coupled to the valve frame. The valve component is then deployed at the native aortic valve such that the valve frame expands from the radially compressed configuration to a radially expanded configuration with a first portion of the valve frame engaging the native aortic valve and a second portion the valve frame engaging the attachment members of the tubular frame member of the anchor stent. In an embodiment, the anchor stent also includes a distal arm component that extends from a second end of the tubular frame member, and the step of deploying the anchor stent includes the distal arm component extending into the brachiocephalic artery.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIGS. 7-15 are schematic illustrations of an embodiment of a method for delivering and deploying a modular prosthetic valve hereof as an aortic valve replacement.

DETAILED DESCRIPTION OF THE INVENTION

Specific embodiments of the present invention are now described with reference to the figures, wherein like reference numbers indicate identical or functionally similar elements. The terms "distal" and "proximal" when used in the following description to refer to a catheter or delivery system are with respect to a position or direction relative to the treating clinician. Thus, "distal" and "distally" refer to positions distant from or in a direction away from the clinician and "proximal" and "proximally" refer to positions near or in a direction toward the clinician. When the terms "distal" and "proximal" are used in the following description to refer to a device to be implanted into a vessel, such as an anchor stent or valve component, they are used with reference to the direction of blood flow from the heart. Thus, "distal" and "distally" refer to positions distant from, or a direction away from the heart and "proximal" and "proximally" refer to positions near to, or a direction towards to the heart.

Figure 1:
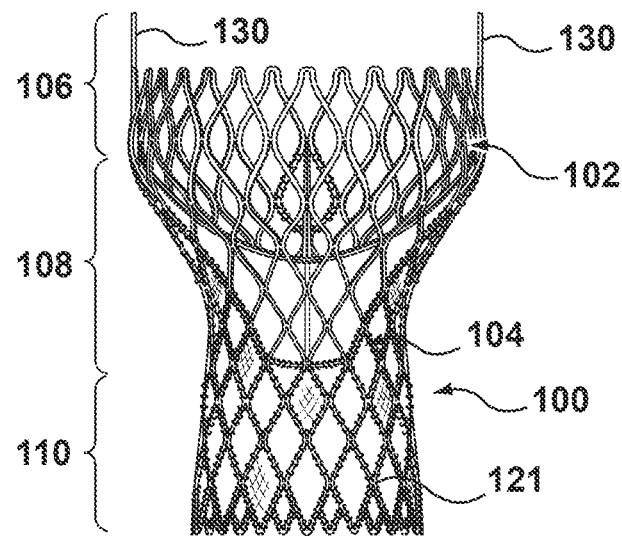
FIG. 1 is a schematic illustration of a prior art stented valve prosthesis.
Figure 2:
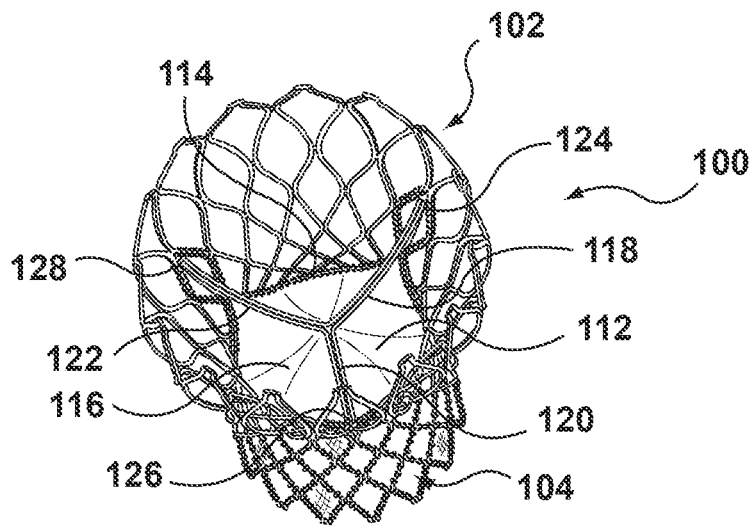
FIG. 2 is a schematic illustration of the prior art stented valve prosthesis of FIG. 1.

FIGS. 1 and 2 show an exemplary conventional valve prosthesis similar to the Medtronic CoreValve® transcatheter aortic valve replacement valve prosthesis and as described in U.S. Patent Application Publication No. 2011/0172765 to Nguyen et al. (hereinafter "the '765 publication"), which is incorporated by reference herein in its entirety. As shown in FIGS. 1 and 2, conventional valve prosthesis 100 includes an expandable frame 102 having a valve body 104 affixed to its interior surface, e.g., by sutures. Frame 102 preferably comprises a self-expanding structure formed by laser cutting or etching a metal alloy tube comprising, for example, stainless steel or a shape memory material such as nickel titanium. The frame has an expanded deployed configuration which is impressed upon the metal alloy tube using techniques known in the art. Valve body 104 preferably comprises individual leaflets assembled to a skirt, where all of the components are formed from a natural or man-made material, including but not limited to, mammalian tissue, such as porcine, equine or bovine pericardium, or a synthetic or polymeric material.

Frame 102 in the exemplary embodiment includes an outflow section 106, and inflow section 110, and a constriction region 108 between the inflow and outflow sections. Frame 102 may comprise a plurality of cells having sizes that vary along the length of the prosthesis. When configured as a replacement for an aortic valve, inflow section 110 extends into and anchors within the aortic annulus of a patient's left ventricle and outflow section 106 is positioned in the patient's ascending aorta. Frame 102 also may include eyelets 130 for use in loading the heart valve prosthesis 100 into a delivery catheter.

Valve body 104 may include a skirt 121 affixed to frame 102, and leaflets 112, 114, 116. Leaflets 112, 114, 116 may be attached are attached along their bases to skirt 121, for example, using sutures or a suitable biocompatible adhesive. Adjoining pairs of leaflets are attached to one another at their lateral ends to form commissures 124, 126, 128, with free edges 118, 120, 122 of the leaflets forming coaptation edges that meet in an area of coaptation, as described in the '765 application and shown in FIG. 2 hereof.

The following detailed description is merely exemplary in nature and is not intended to limit the invention or the application and uses of the invention. Although the description of the invention is in the context of transcatheter aortic valve implantation, the invention may also be used in any other body passageways where it is deemed useful. Furthermore, there is no intention to be bound by any expressed or implied theory presented in the preceding technical field, background, brief summary or the following detailed description.

Embodiments hereof are related to a modular valve prosthesis including an anchor stent and a valve component. In an embodiment shown in FIG. 3-5, a modular valve prosthesis 200 includes an anchor stent 210 and a valve component 240. Valve component 240 is sized and shaped to fit within a lumen of anchor stent 210, as described in more detail below.

Figure 3:
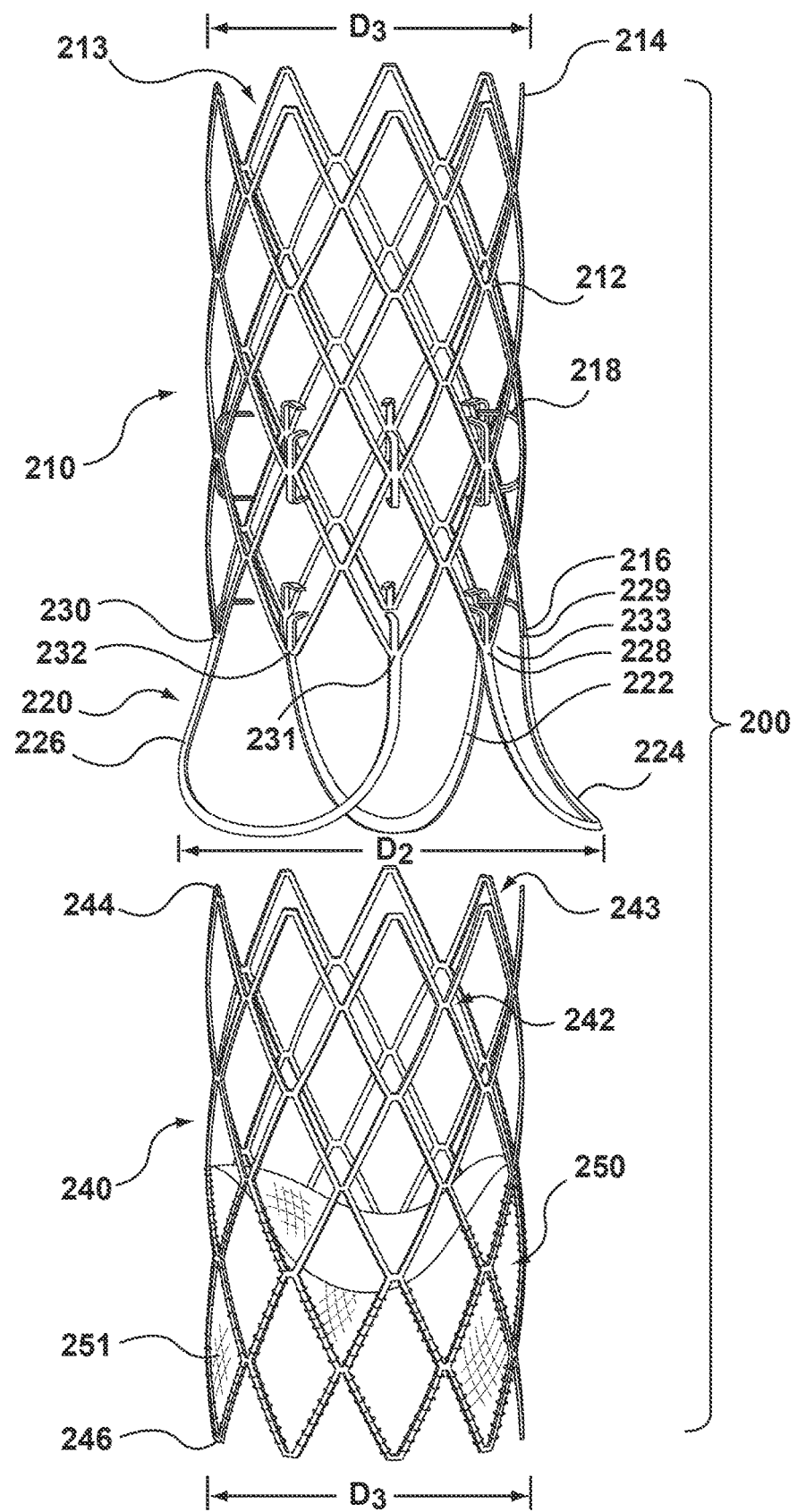
FIG. 3 is a schematic illustration of modular valve prosthesis in accordance with an embodiment hereof.
Figure 4A:
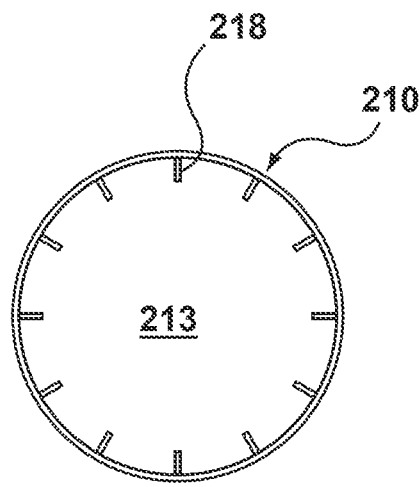
FIG. 4A is another embodiment of a schematic top view of the anchor stent of FIG. 3.
Figure 4:
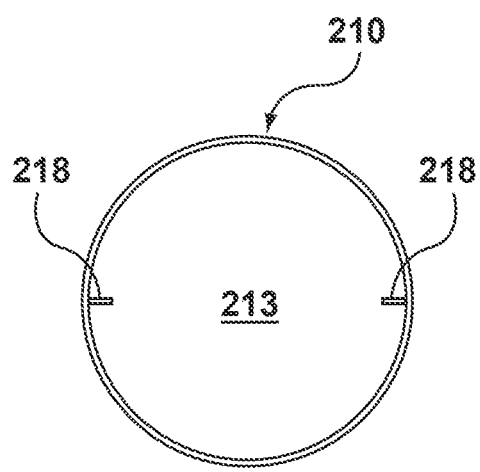
FIG. 4 is an embodiment of a schematic top view of the anchor stent of FIG. 3

Anchor stent 210 includes a frame 212 having a proximal end 216 and a distal end 214, and a proximal arm component 220 extending proximally from proximal end 216 of frame 212, as shown in FIG. 3. Frame 212 is a generally tubular configuration having a lumen 213. Frame 212 is a stent structure as is known in the art, as described in more detail below. Frame 212 may be self expanding or may be balloon expandable. Generally, frame 212 includes a first, radially compressed configuration for delivery and a second, radially expanded or deployed configuration when deployed at the desired site. In the radially expanded configuration, frame 212 has a diameter $D_1$ in the range of 23 to 31 millimeters. However, those skilled in the art would recognize that frame 212 may have a smaller or larger expanded diameter $D_1$ depending on the application. Further, as known those skilled in the art, the unrestrained expanded diameter of self-expanding frames, such as frame 212, is generally about 2 millimeters larger than the diameter of the vessel in which the frame is to be installed, in order to create opposing radial forces between the outward radial force of the frame against an inward resisting force of the vessel. Frame 212 may further include attachment members 218 extending radially inward from an interior surface of frame 212. Attachment members 218 may be barbs, hooks, loops, or any other mechanism for coupling to the frame of valve component 240, as described in more detail below. Attachment members 218 may extend around the entire inner circumference of frame 212, as shown in FIG. 4A, on opposite sides of the inner circumference of frame 212, as shown in FIG. 4, or any other distribution desired by those skilled in the art. Further, several rows of attachment members 218 may be included, as shown in FIG. 3. As explained in detail below, including several rows of attachment members 218 allows for less precision in placing anchor stent 210 in the anatomy and also allows for a single size or a limited range of sizes for the frame of valve component 240 to be used in anatomies of various sizes.

Proximal arm component 220 extends proximally from proximal end 216 of frame 212. In the embodiment shown in FIG. 3, proximal arm component 220 includes a first arm 222, a second arm 224, and a third arm 226. In the embodiment shown in FIG. 3, each arm 222, 224, 226 is in the form of a wire loop with first and second ends of the wire attached to frame 212. In particular, first arm 222 includes first and second ends attached to frame 212 at connections 232, 233 respectively. Similarly, second arm 224 includes first and second ends attached to frame 212 at connections 228, 229, respectively, and third arm 226 includes first and second ends attached to frame 212 at connections 230, 231, respectively. Connections 228, 229, 230, 231, 232, 233 may be formed by the material of the arms and frame 212 fused or welded together. Alternatively, the connections may be mechanical connections such as, but not limited to, sutured or otherwise tied, a crimp to crimp ends of the arms to frame 212, as known to those skilled in the art. Other types of connections, as known to those skilled in the art, may also be used. Proximal arm component 220 includes a radially compressed configuration for delivery to the treatment site and a radially expanded or deployed configuration. In the radially expanded configuration, proximal arm component has a diameter $D_2$ in the range of 29 to 39 mm. However, those skilled in the art would recognize that diameter $D_2$ may be smaller or larger depending on the application. As shown in FIG. 3, in the radially expanded configuration, arms 222, 224, and 226 flare outwardly from proximal end 216 of frame 212, such that $D_2$ is larger than $D_1$. Although proximal arm component 220 has been shown as having three arms with connections approximately equally spaced around the circumference of frame 212, it would be understood by those skilled in the art that more or less arms may be utilized, and that the arms need not be equally spaced around the circumference of frame 212.

Valve component 240 includes a frame 242 and a prosthetic valve 250. Frame 242 is a generally tubular configuration having a proximal end 246, a distal end 244, and a lumen 243 therebetween. Frame 242 is a stent structure as is known in the art, as described in more detail below. Frame 242 may be self expanding or may be balloon expandable. Generally, frame 242 includes a first, radially compressed configuration for delivery and a second, radially expanded or deployed configuration when deployed at the desired site. In the radially expanded configuration, frame 242 has a diameter $D_3$ in the range of 23 to 31 millimeters. However, those skilled in the art would recognize that frame 242 may have a smaller or larger expanded diameter $D_3$ depending on the application.

Figure 5:
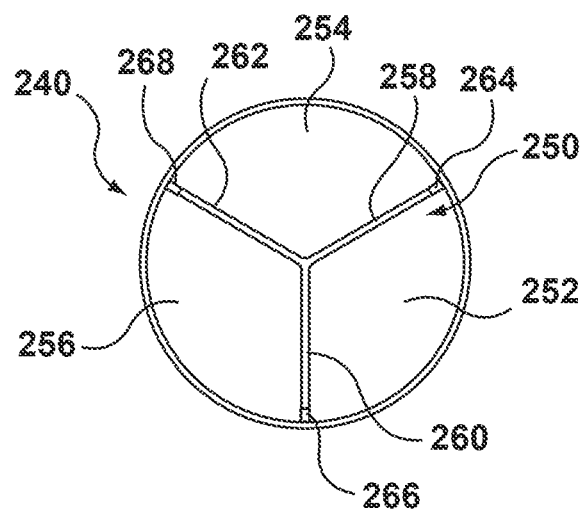
FIG. 5 is a schematic illustration of the valve leaflets of the valve component of FIG. 3.

Valve component 240 further includes a prosthetic valve 250 attached to frame 242. Prosthetic valve 250 may include a skirt 251 affixed to frame 242 as described above with respect to FIGS. 1-2. Prosthetic valve 250 includes prosthetic valve leaflets 252, 254, 256, as shown in FIG. 5. Leaflets 252, 254, 254 may be attached along their bases to skirt 251, for example, using sutures or a suitable biocompatible adhesive, or may be attached to frame 242 in other ways known to those skilled in the art. Adjoining pairs of leaflets are attached to one another at their lateral ends to form commissures 264, 266, 268, with free edges 258, 260, 262 of the leaflets forming coaptation edges that meet in an area of coaptation, similar to as described in the '765 application. However, those skilled in the art would recognize that any suitable prosthetic valve design may be used in the present embodiment of prosthetic valve 250.

Frames 212 and 242, as described above, are generally stent structures. Such stent structures may comprise a number of strut or wire portions arranged relative to each other to provide a desired compressibility, strength, and leaflet attachment zone(s) to the heart valve. In general terms, frames 212, 242 are generally tubular support structures, and leaflets will be secured to frame 242 to provide a stented prosthetic valve. The prosthetic valve leaflets 252, 254, 256 can be formed from a variety of materials, such as autologous tissue, xenograph material, or synthetics as are known in the art. The leaflets may be provided as a homogenous, biological valve structure, such as a porcine, bovine, or equine valve. Alternatively, the leaflets can be provided independent of one another (e.g., bovine or equine pericardial leaflets) and subsequently assembled to the support structure of the frame 242. In another alternative, the stent and leaflets can be fabricated at the same time, such as may be accomplished using high strength nano-manufactured NiTi films of the type produced at Advanced Bio Prosthetic Surfaces Ltd. (ABPS) of San Antonio, Tex., for example. Frame 242 is generally configured to accommodate three leaflets; however, the replacement prosthetic heart valves of the invention can incorporate more or less than three leaflets.

In more general terms, the combination of a frame with one or more leaflets can assume a variety of other configurations that differ from those shown and described, including any known prosthetic heart valve design. In certain embodiments of the invention, frame 242 with leaflets 252, 254, 256 may utilize certain features of known expandable prosthetic heart valve configurations, whether balloon expandable, self-expanding, or unfurling (as described, for example, in U.S. Pat. Nos. 3,671,979; 4,056,854; 4,994,077; 5,332,402; 5,370,685; 5,397,351; 5,554,185; 5,855,601; and 6,168,614; U.S. Patent Application Publication No. 2004/0034411; Bonhoeffer P., et al., "Percutaneous Insertion of the Pulmonary Valve", Pediatric Cardiology, 2002; 39:1664-1669; Anderson H R, et al., "Transluminal Implantation of Artificial Heart Valves", EUR Heart J., 1992; 13:704-708; Anderson, J. R., et al., "Transluminal Catheter Implantation of New Expandable Artificial Cardiac Valve", EUR Heart J., 1990, 11: (Suppl) 224a; Hilbert S. L., "Evaluation of Explanted Polyurethane Trileaflet Cardiac Valve Prosthesis", J Thorac Cardiovascular Surgery, 1989; 94:419-29; Block P C, "Clinical and Hemodynamic Follow-Up After Percutaneous Aortic Valvuloplasty in the Elderly", The American Journal of Cardiology, Vol. 62, Oct. 1, 1998; Boudjemline, Y., "Steps Toward Percutaneous Aortic Valve Replacement", Circulation, 2002; 105:775-558; Bonhoeffer, P., "Transcatheter Implantation of a Bovine Valve in Pulmonary Position, a Lamb Study", Circulation, 2000: 102: 813-816; Boudjemline, Y., "Percutaneous Implantation of a Valve in the Descending Aorta In Lambs", EUR Heart J, 2002; 23:1045-1049; Kulkinski, D., "Future Horizons in Surgical Aortic Valve Replacement: Lessons Learned During the Early Stages of Developing a Transluminal Implantation Technique", ASAIO J, 2004; 50:364-68; the teachings of which are all incorporated herein by reference).

Figure 6:
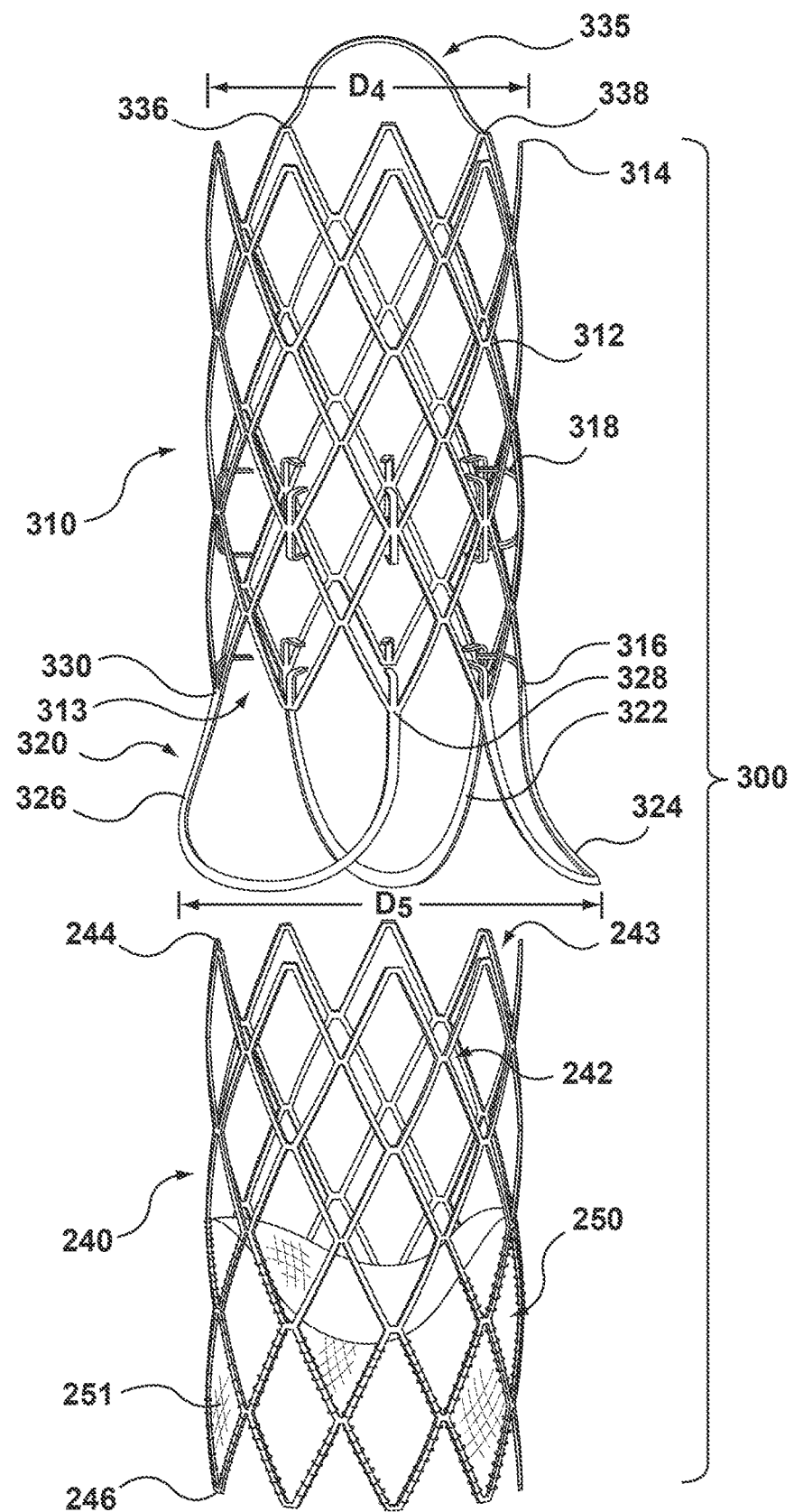
FIG. 6 is a schematic illustration of modular valve prosthesis in accordance with another embodiment hereof.

FIG. 6 shows an embodiment of modular valve prosthesis 300 including an anchor stent 310 and a valve component 240. Valve component 240 is sized and shaped to fit within a lumen of anchor stent 310, as described in more detail below.

Anchor stent 310 includes a frame 312 having a proximal end 316 and a distal end 314, a proximal arm component 320 extending proximally from proximal end 316 of frame 312, and a distal arm component 335 extending distally from distal end 314 of frame 312, as shown in FIG. 6. Frame 312 is a generally tubular configuration having a lumen 313. Frame 312 is a stent structure as is known in the art, as described in more detail above. Frame 312 may be self expanding or may be balloon expandable. Generally, frame 312 includes a first, radially compressed configuration for delivery and a second, radially expanded or deployed configuration when deployed at the desired site. In the radially expanded configuration, frame 312 has a diameter $D_4$ in the range of 23 to 31 millimeters. However, those skilled in the art would recognize that frame 312 may have a smaller or larger expanded diameter D4 depending on the application. Frame 312 further includes attachment members 318 extending radially inward from an interior surface of frame 312. Attachment members 318 may be barbs, hooks, loops, or any other mechanism for coupling to the frame of valve component 340, as described in more detail below. Attachment members 318 may extend around the entire inner circumference of frame 312, on opposite sides of the inner circumference of frame 312, or any other distribution desired by those skilled in the art. Further, several rows of attachment members 318 may be included, as shown in FIG. 3. As explained in detail below, including several rows of attachment members 318 allows for less precision in placing anchor stent 310 in the anatomy and also allows for a single size or a limited range of sizes for frame of valve component 240 to be used in anatomies of various sizes.

Proximal arm component 320 extends proximally from proximal end 316 of frame 312. In the embodiment shown in FIG. 6, proximal arm component 320 includes a first arm 322, a second arm 324, and a third arm 326. In the embodiment shown in FIG. 6, each arm 322, 324, 326 is in the form of a wire loop with first and second ends of the wire attached to frame 312. In particular, third arm 326 includes first and second ends attached to frame 312 at connections 328, 330, respectively. Similarly, first arm 322 and second arm 324 include first and second connections as described above with respect to FIG. 3. Connections 328, 330, and connections of the other arms to frame 312 may be formed by the material of the arms and frame 312 fused or welded together. Alternatively, the connections may be mechanical connections such as, but not limited to, sutured or otherwise tied, a crimp to crimp ends of the arms to frame 312, as known to those skilled in the art. Other types of connections, as known to those skilled in the art, may also be used. Proximal arm component 320 includes a radially compressed configuration for delivery to the treatment site and a radially expanded or deployed configuration. In the radially expanded configuration, proximal arm component has a diameter $D_5$ in the range of 29 to 39 mm. However, those skilled in the art would recognize that diameter D5 may be smaller or larger depending on the application. As shown in FIG. 6, in the radially expanded configuration, arms 322, 324, and 326 flare outwardly from proximal end 316 of frame 312, such that $D_5$ is larger than $D_4$. Although proximal arm component 320 has been shown as having three arms with connections approximately equally spaced around the circumference of frame 312, it would be understood by those skilled in the art that more or less arms may be utilized, and that the arms need not be equally spaced around the circumference of frame 312.

Distal arm component 335 extends distally from distal end 316 of frame 312. In the embodiment shown in FIG. 6, distal arm component 335 is a single arm in the form of a wire loop with first and second ends of the wire attached to frame 312. In particular, distal arm component 335 includes first and second ends attached to frame 312 at connections 336, 338, respectively. Connections 336, 338 may be formed by the material of the arms and frame 312 fused or welded together. Alternatively, the connections may be mechanical connections such as, but not limited to, a crimp to crimp ends of the arm to frame 312, as known to those skilled in the art. Other types of connections, as known to those skilled in the art, may also be used. Distal component 335 includes a radially compressed configuration for delivery to the treatment site and a radially expanded or deployed configuration. In the radially expanded configuration, distal arm component 335 flares outwardly from distal end 316 of frame 312. Distal arm component 335 is configured to be deployed within a branch vessel branching from the aortic arch, such as the brachiocephalic artery, as described in more detail below.

Valve component 240 shown in FIG. 6 is the same as valve component 240 described above with respect to FIG. 3 and FIG. 5. Accordingly, it will not be described again here. Thus, valve component 240 of FIG. 6 may be valve component 240 as described above, including all variations described above with respect to valve component 240.

As explained briefly above and in more detail below. Modular valve prosthesis 200 or 300 includes an anchor stent 210/310 and a valve component 240. Anchor stent 21/310 is configured to be disposed in the aorta, with proximal arm component 220/320 extending into the aortic root or aortic sinuses 412. Valve component 240 is configured to be disposed such that prosthetic valve 250 is disposed approximately at the location of the native aortic valve with proximal end 246 of frame 242 separating the valve leaflets of the native aortic valve. Distal end 244 of frame 242 extends into lumen 213/313 of frame 212/312 of anchor stent 210/310 and is held in place by attachment members 218/318. Further, proximal arm component 220/320 and distal arm component 335 of anchor stent 210/310 provide support for anchor stent 210/310 within the aorta. Accordingly, by utilizing such a modular device, anchor stent 210/310 provides the necessary radial force as assisted by the proximal and distal arm components to hold valve component 240 in place. This permits frame 242 of valve component 240 to have less radial force than conventional prosthetic valves which require sufficient radial force to hold the prosthetic valve within the aorta. Such a conventional prosthetic valve, in order to provide sufficient radial force, requires a bulkier stent frame, thereby resulting in a larger delivery profile. Further, utilizing distal and/or proximal arm components on anchor stent 210/310 allows the anchor stent to have a smaller delivery profile because the arm components assist the radial force of frame 212/312 in supporting the anchor stent 210/310 in the aorta.

FIGS. 7-15 schematically represent a method of delivering and deploying a modular valve prosthesis in accordance with an embodiment hereof. FIGS. 7-13 describe the method with respect to modular valve prosthesis 200 of FIGS. 3-5. However, the method applies equally to modular valve prosthesis 300 of FIG. 6. FIG. 14 is the equivalent of FIG. 10 but showing anchor stent 310 deployed in the aorta. Further, FIG. 15 is the equivalent of FIG. 13 but showing modular valve prosthesis 300 fully deployed.

Figure 7:
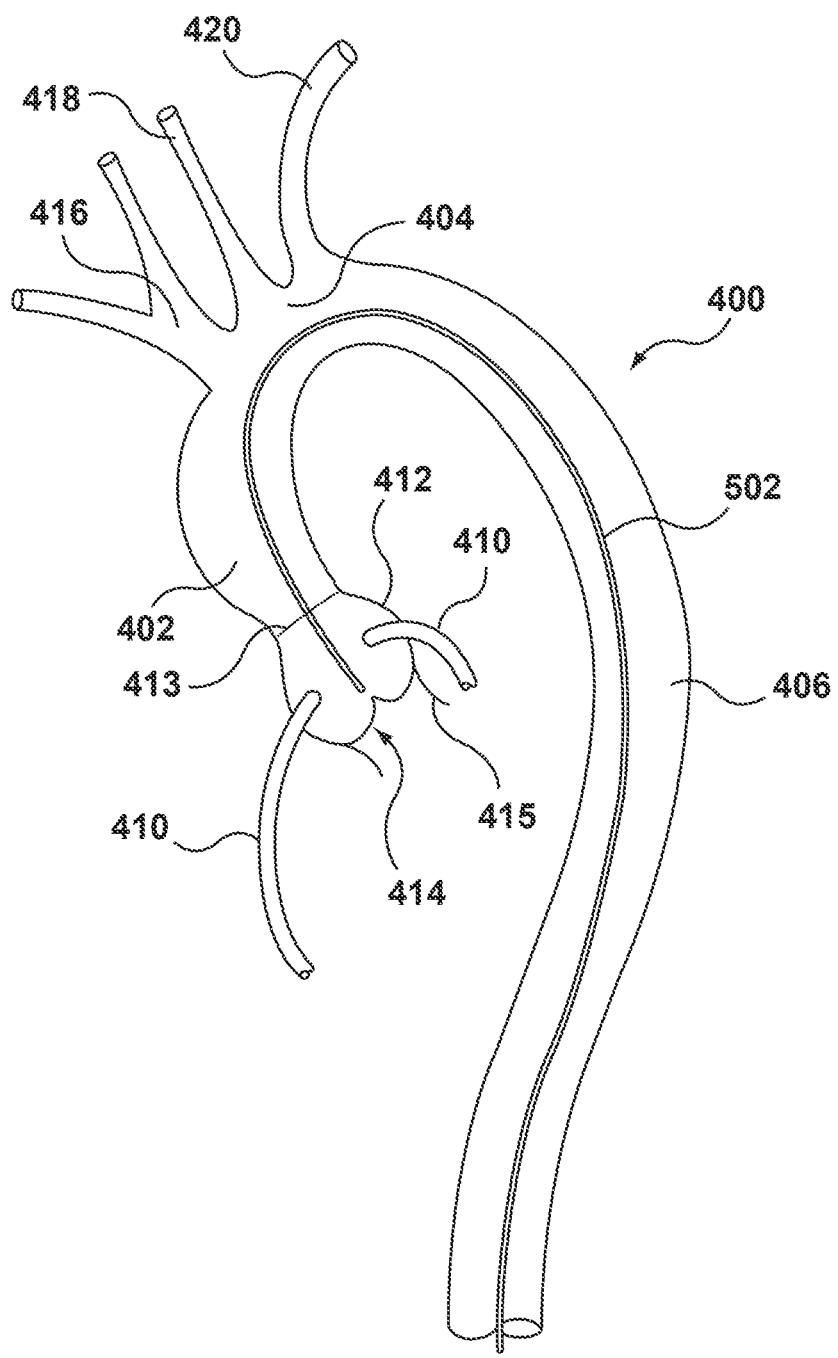

FIG. 7 shows a guidewire 502 advanced through the aorta 400 into the aortic sinuses 412 in the region of the aortic valve 414. Guidewire 502 may be introduced through an opening or arteriotomy through the wall of femoral artery in the groin region of the patient by methods known to those skilled in the art, such as, but not limited to, the Seldinger technique. Guidewire 502 is advanced into the descending (or abdominal) aorta 406, the aortic arch 404, and the ascending aorta 402, as shown in FIG. 7. FIG. 7 also shows three branch arteries emanating from the aortic arch 404. In particular, the innominate or brachiocephalic artery 416, the left common carotid artery 418, and the left subclavian artery 420 emanate from the aortic arch 404. The brachiocephalic artery 416 branches into the right common carotid artery and the right subclavian artery.

FIG. 8 shows a delivery system 500 for delivering anchor stent 210 being advanced over guidewire 502 to a location in the ascending aorta 402. Delivery system 500 may be any suitable delivery system known to those skilled in the art for delivery stents and/or stent grafts. In the embodiment shown schematically, anchor stent 210 is a self-expanding stent. Accordingly, delivery system 500 generally includes an inner or guidewire shaft 508 which includes a guidewire lumen for receiving guidewire 502. As is known to those skilled in the art, a proximal end of guidewire 502 may be backloaded into the guidewire lumen of inner shaft 508 through a distal opening in inner shaft 508. As known to those skilled in the art, delivery system 500 may be an over-the-wire type catheter, or a rapid exchange catheter, or other known catheter devices. Delivery system 500 further generally includes an outer sheath 504 that maintains anchor stent 210 in the radially compressed or delivery configuration during intraluminal delivery through the vasculature, as shown in FIG. 8. Delivery system 500 may also include a pusher or stopper 506, and other features known to those skilled in the art. Delivery system 500 and/or anchor stent 210 may also include, for example, radiopaque markers such that the clinician may determine when delivery system 500 and/or anchor stent 210 is in the proper location for deployment.

Once delivery system 500 has been advanced to the desired location, such as when proximal end 216 of anchor stent is generally aligned with the sinotubular junction 413, outer sheath 504 is retracted proximally, i.e., towards the clinician, as shown in FIG. 9. As outer sheath 504 is retracted, proximal arm component 220 expands radially, engaging the aortic sinuses 412, and frame 212 of anchor stent 210 also begins to expand radially outward, engaging the inner wall of the ascending aorta, as shown in FIG. 9. In another embodiment, outer sheath 504 is partially retracted in a position several millimeters proximal to leaflets 414 such that proximal arm component 220 is allowed to expand near the sinotubular junction 413. Delivery system 500 is then advanced those several millimeters to allow proximal arm component 220 to seat in the more distal position shown in FIG. 9. Further, although proximal arm component 220 is shown in FIGS. 9-15 as having arms 222, 224, 226 extending to an area near the base of leaflets 414, those skilled in the art would recognize that arms 222, 224, 226 may be shorter such that they engage the sinuses 412 at a location nearer to sinotubular junction 413 than shown in FIGS. 9-15. Those skilled in the art would also recognize that FIGS. 3, 6, and 9-15 are not drawn to scale regarding the relative lengths of anchor stent 210, proximal arm component 220, and valve component 240.

Outer sheath 504 continues to be retracted until anchor stent 210 is fully deployed, as shown in FIG. 10. As can be seen in FIG. 10, proximal arm component 220 is in the radially expanded configuration such that it flares outwardly from frame 212 and engages the aortic sinuses 412, and frame 212 is in the radially expanded configuration such that it engages the inner wall of the ascending aorta 402. Similarly, if anchor stent 310 were deployed in accordance with the steps described above, it would result in a deployed anchor stent 310, with proximal arm component 320 in the radially expanded configuration such that it flares outwardly from frame 312 and engages the aortic sinuses 412, frame 312 is in the radially expanded configuration such that it engages the inner wall of the ascending aorta 402, and distal arm component 335 in the radially expanded configuration such that it engages the brachiocephalic artery 416, as shown in FIG. 14.

With anchor stent 210 deployed and delivery system removed from the patient, a second delivery system 550 is advanced over guidewire 502, as shown schematically in FIG. 11. Second delivery system 550 includes valve component 240 disposed therein in a radially compressed or delivery configuration. Second delivery system 550 may be any suitable delivery system known to those skilled in the art for delivery stents, stent grafts, or stented prosthetic valves. In the embodiment shown schematically, frame 242 of valve component 240 is a self-expanding stent. Accordingly, second delivery system 550 may be a delivery system generally used for self expanding stents. As shown schematically, second delivery system includes an inner or guidewire shaft 558 which includes a guidewire lumen for receiving guidewire 502. As is known to those skilled in the art, a proximal end of guidewire 502 may be backloaded into the guidewire lumen of inner shaft 558 through a distal opening in inner shaft 558. As known to those skilled in the art, second delivery system 550 may be an over-the-wire type catheter, or a rapid exchange catheter, or other known catheter devices. Second delivery system 550 further generally includes an outer sheath 554 that maintains valve component 240 in the radially compressed or delivery configuration during intraluminal delivery through the vasculature, as shown in FIG. 11. Second delivery system 550 may also include a pusher or stopper 556, and other features known to those skilled in the art. Second delivery system 550 and/or valve component 240 may also include, for example, radiopaque markers such that the interventionalist may determine when second delivery system 550 and/or valve component is in the proper location for deployment.

Second delivery system 550 is advanced over guidewire 502 until second delivery system with valve component 240 is at a desired location, such as a distal end of second delivery system 550 being disposed through the native aortic valve leaflets 414 and proximal end 246 of frame 242 being generally aligned with the aortic annulus 415, as shown in FIG. 11. Those skilled in the art would recognize that this is only an example of a possible desired location and that other desired locations may be used. Once second delivery system 550 has been advanced to the desired location, outer sheath 554 is retracted proximally, i.e., towards the clinician, as shown in FIG. 12. As outer sheath 554 is refracted, frame 242 of valve component expands radially outward to the radially expanded or deployed configuration, as shown in FIG. 12. As frame 242 expands, frame 242 separated native valve leaflets 414, as shown in FIG. 12.

Outer sheath 554 continues to be retracted until frame 242 of valve component 240 is fully deployed, as shown in FIG. 13. As can be seen in FIG. 13, distal end 244 of frame 242 is disposed in lumen 213 of anchor stent 210. Accordingly, a portion of frame 242 disposed in lumen 213 engages attachment members 218 of anchor stent 210. Anchor stent 210 thereby provides support for frame 242 of valve component 240, thereby allowing frame 242 to provide less radially outward force than conventional stented prostheses that rely on such radial force to support the stented valve. As can be seen in FIG. 13, with frame 242 of valve component coupled to anchor stent 210 through attachment members 218, prosthetic valve 250 is generally disposed between native valve leaflets 414 and operates to replace the operation of native valve leaflets 414.

FIG. 15 shows valve component 240 deployed within anchor stent 310 of modular valve prosthesis 300 of the embodiment of FIG. 6. The steps described above to deliver and deploy valve component 240 through anchor stent 210 apply equally to deploy valve component 240 through anchor stent 310.

Figure 16:
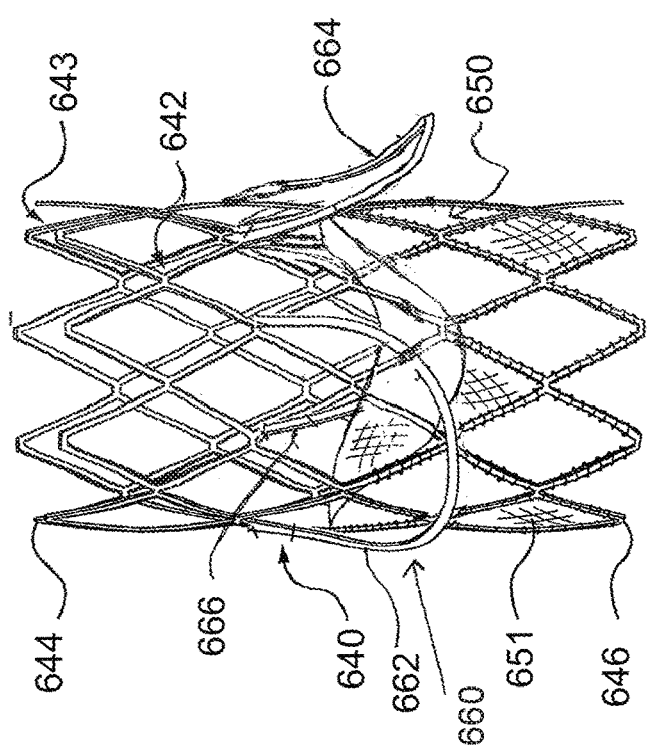
FIG. 16 is a schematic illustration of an embodiment of a valve component with a valve arm component.

FIG. 16 shows another embodiment of a valve component 640. Valve component 640 may be used with an anchor stent 210, 310 as shown in FIGS. 3 and 6 or other similar anchor stent. Valve component 640 includes a frame 642 and a prosthetic valve 650. Frame 642 is a generally tubular configuration having a proximal end 646, a distal end 644, and a lumen 643 therebetween. Frame 642 is a stent structure as is known in the art, as described in more detail above. Frame 642 may be self expanding or may be balloon expandable. Generally, frame 642 includes a first, radially compressed configuration for delivery and a second, radially expanded or deployed configuration when deployed at the desired site. In the radially expanded configuration, frame 642 has a diameter in the range of 23 to 31 millimeters. However, those skilled in the art would recognize that frame 642 may have a smaller or larger expanded diameter depending on the application.

Valve component 640 further includes a prosthetic valve 650 attached to frame 642. Prosthetic valve 650 may include a skirt 651 affixed to frame 642 as described above with respect to FIGS. 1-2. Prosthetic valve 650 includes prosthetic valve leaflets, as described above. However, those skilled in the art would recognize that any suitable prosthetic valve design may be used in the present embodiment of prosthetic valve 650.

Figure 17:
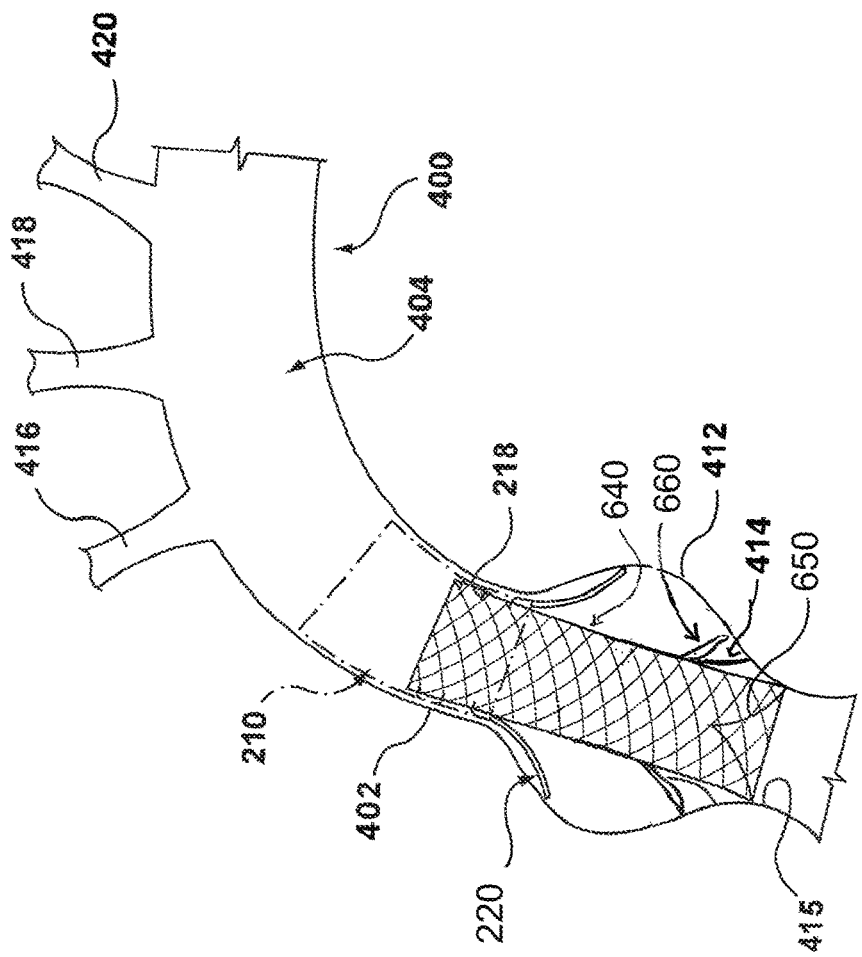
FIG. 17 is a schematic illustration of the valve component of FIG. 17 deployed in the anchor stent of FIG. 3 as an aortic valve replacement.

Valve component 640 further includes a valve arm component 660 extending proximally from a periphery of frame 642. Valve arm component is attached to the periphery of frame 642 in a middle portion of valve component 640 between proximal end 646 and distal end 644. In the embodiment shown in FIG. 16, valve arm component 660 is attached to frame 642 at a location distal of prosthetic valve 650. However, those skilled in the art would recognize that the precise location of valve arm component 660 may be varied without departing from the spirit and scope of the present description. Valve arm component 660 includes a first arm 662, a second arm 664, and a third arm 666. In the embodiment shown in FIG. 16, each arm 662, 664, 666 is in the form of a wire loop with first and second ends of the wire attached to frame 642, as described above with respect to proximal arm components 220, 320. However, those skilled in the art would recognize that other types and constructions of valve arm component 660 may be used. Valve arm component 660 includes a radially compressed configuration for delivery to the treatment site and a radially expanded or deployed configuration. As shown in FIG. 17, described in more detail below, arms 662, 664, and 666 flare outwardly from frame 642. Although valve arm component 660 has been shown as having three arms with connections approximately equally spaced around the circumference of frame 642, it would be understood by those skilled in the art that more or less arms may be utilized, and that the arms need not be equally spaced around the circumference of frame 642.

FIG. 17 shows valve component 640 of FIG. 16 deployed within anchor stent 210 of modular valve prosthesis 200 of the embodiment of FIG. 3. However, as can be seen in FIG. 17, proximal arm component 220 of anchor stent 210 in the embodiment of FIG. 17 is shorter than the embodiment shown in FIGS. 9-15. As can be seen in FIG. 17, proximal arm component 220 of anchor stent 210 assists in preventing distal movement of anchor stent 210 (i.e. away from valve 414), and valve component 640 coupled thereto, because proximal arm component 220 abuts the wall of the sinuses 412 in the distal direction. Further, valve arm component 660 assists in preventing proximal movement of valve component 640 by engaging the sinuses 412 near a base of native valve 414. Thus, anchor stent 210 and valve component 640 do not require as much radial force to maintain valve component 640 in the desired location than if proximal arm component 220 and valve arm component 660 were not utilized. The steps described above to deliver and deploy valve component 240 through anchor stent 210 apply equally to deploy valve component 640 through anchor stent 210. Further, anchor stent 310 may be used instead of anchor stent 210.

Figure 18:
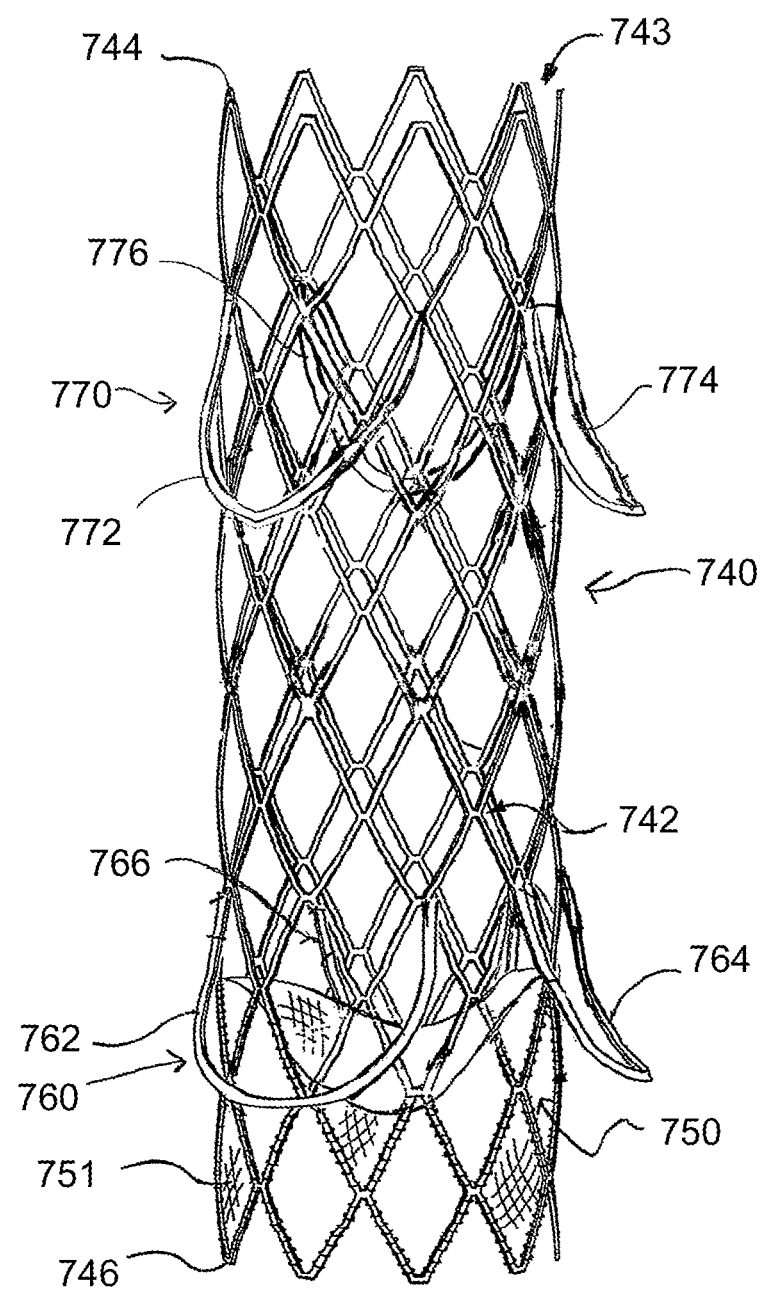
FIG. 18 is a schematic illustration of an embodiment of a valve component with a pair of valve arm components.

FIG. 18 shows another embodiment of a valve component 740. In the embodiment of FIG. 18, valve component 740 need not be used with an anchor stent as described above, although it may be used with an anchor stent if desired. Valve component 740 includes a frame 742 and a prosthetic valve 750. Frame 742 is a generally tubular configuration having a proximal end 746, a distal end 744, and a lumen 743 therebetween. Frame 742 is a stent structure as is known in the art, as described in more detail above. Frame 742 may be self expanding or may be balloon expandable. Generally, frame 742 includes a first, radially compressed configuration for delivery and a second, radially expanded or deployed configuration when deployed at the desired site. In the radially expanded configuration, frame 742 has a diameter in the range of 23 to 31 millimeters. However, those skilled in the art would recognize that frame 742 may have a smaller or larger expanded diameter depending on the application.

Valve component 740 further includes a prosthetic valve 750 attached to frame 742. Prosthetic valve 750 may include a skirt 751 affixed to frame 742 as described above with respect to FIGS. 1-2. Prosthetic valve 750 includes prosthetic valve leaflets, as described above. However, those skilled in the art would recognize that any suitable prosthetic valve design may be used in the present embodiment of prosthetic valve 750.

Figure 19:
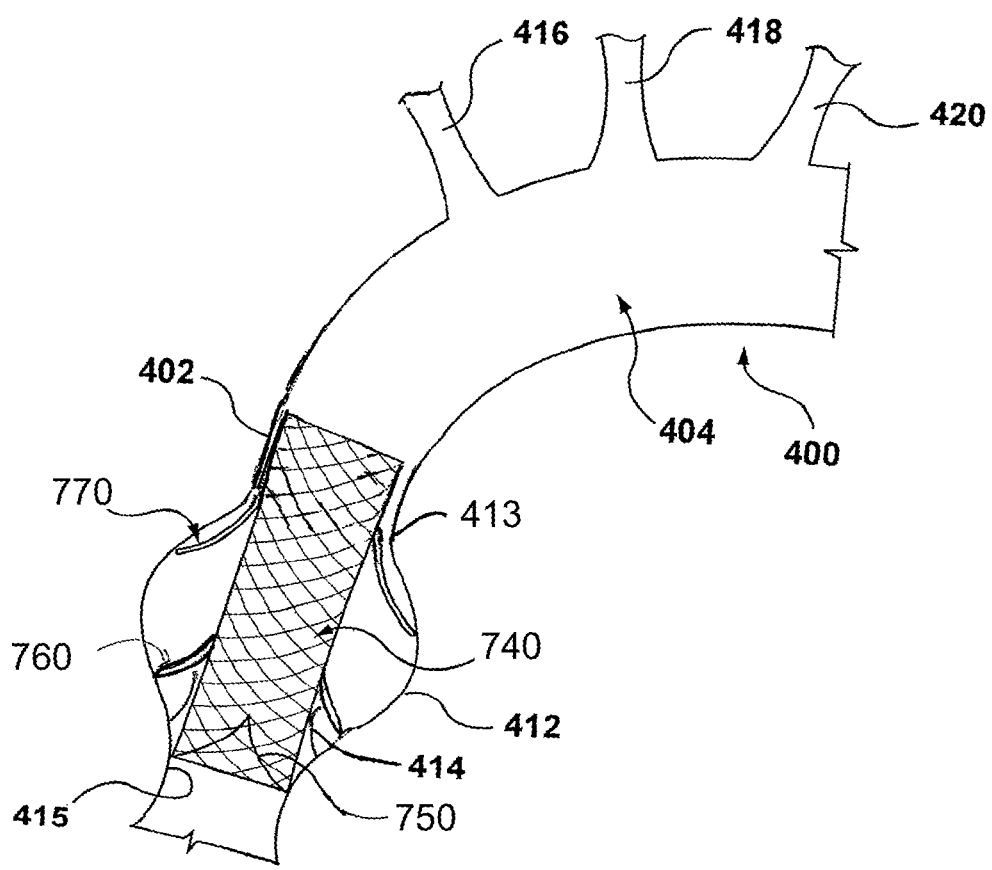
FIG. 19 is a schematic illustration of the valve component of FIG. 18 deployed in as an aortic valve replacement without the use of an anchor stent.

Valve component 740 further includes a proximal valve arm component 760 and a distal valve arm component 770, each extending proximally from a periphery of frame 742. Proximal valve arm component 760 is similar to valve arm component 660 of FIGS. 16-17, and is attached to the periphery of frame 742 in a middle portion of valve component 740 between proximal end 746 and distal end 744. In the embodiment shown in FIG. 18, proximal valve arm component 760 is attached to frame 742 at a location distal of prosthetic valve 750, but near prosthetic valve 750. However, those skilled in the art would recognize that the precise location of proximal valve arm component 760 may be varied without departing from the spirit and scope of the present description. Distal valve arm component is similar to proximal arm component 220, 320 described above. Distal valve arm component 770 is attached to the periphery of frame 742 in a middle portion of valve component 740 between proximal end 746 and distal end 744, distal of proximal valve arm component 760. In the embodiment shown in FIG. 18, distal valve arm component 770 is attached to frame 742 at a location near distal end 746. However, those skilled in the art would recognize that the precise location of distal valve arm component 770 may be varied without departing from the spirit and scope of the present description. Each of proximal and distal valve arm components 760, 770 includes a first arm 762, 772, a second arm 764, 774, and a third arm 766, 776. In the embodiment shown in FIG. 18, each arm 762, 772, 764, 774, 766, 776 is in the form of a wire loop with first and second ends of the wire attached to frame 742, as described above with respect to proximal arm components 220, 320. However, those skilled in the art would recognize that other types and constructions of proximal and distal valve arm components 760, 770 may be used. Proximal and distal valve arm components 760, 770 each include a radially compressed configuration for delivery to the treatment site and a radially expanded or deployed configuration. As shown in FIG. 19, described in more detail below, arms 762, 764, 766 and 772, 774, 776 flare outwardly from frame 742. Although proximal and distal valve arm components 760, 770 have been shown as having three arms with connections approximately equally spaced around the circumference of frame 742, it would be understood by those skilled in the art that more or less arms may be utilized, and that the arms need not be equally spaced around the circumference of frame 742.

FIG. 19 shows valve component 740 of FIG. 18 deployed at the location of native aortic valve 414. As can be seen in FIG. 19, valve component 740 is not deployed within an anchor stent. The steps described above to deliver and deploy valve component 240 apply equally to deploy valve component 740 except that valve component 740 does not need to be delivered through an anchor stent. As can be seen in FIG. 19, distal valve arm component 770 is deployed to engage the area of sinuses 412 adjacent sinotubular junction 413, similar to proximal arm component 220 of anchor stent 210 in FIG. 17. Further, proximal valve arm component 760 is similar to valve arm component 660 of FIGS. 16-17 and engages an area of the sinuses 412 near the bases of native valve 414. Thus, distal valve arm component 770 assists in preventing distal movement of valve component 740 (i.e. away from valve 414) because such distal movement is prevented by distal valve arm component 770 abutting the sinuses 412. Further, proximal valve arm component 760 assists in preventing proximal movement of valve component 740 because such proximal movement is prevented by proximal valve component abutting the sinuses 412 near a base of native valve 414. Thus, valve component 740 does not require as much radial force to maintain valve component 740 in the desired location than if proximal and distal valve arm component 760, 770 were not utilized.

Some examples of advantages of modular valve prostheses described have been described above. These will be summarized and other advantages will also be described. As noted above, because the frame of the valve component is coupled to attachment members of the anchor stent, the frame does not need to support the valve component in the vessel on its own. This allows the valve component to have a smaller delivery profile, thereby enabling the valve component to be used in patients with tortuous or diseased vessels that cannot be navigated with larger delivery devices. Further, the arm components of the anchor stent and/or the valve component provide support such that anchor stent and/or valve component can be of a smaller delivery profile, thereby enabling the anchor stent and or valve component to be used in patients with tortuous or diseased vessels that cannot be navigated with larger delivery devices. For example, and not by way of limitation, anchor stent 210/310 and valve component 240 may each be delivered in a 14 Fr or possibly smaller system, whereas conventional transcatheter aortic valve implantations require an 18 French system.

Further, as explained above, anchor stent 210/310 may include several rows of attachment members 218/318. Accordingly, for coupling to anchor stent 210/310, precise placement of valve component 240 is less important. In other words, the longitudinal location of valve component 240 may vary up to several mm without adverse affect. In conventional stented valves, the stent or frame must often be positioned at a very specific location in order for the frame to properly support the valve prosthesis. Such precise location may be difficult to obtain and may cause an extended time period where blood flow is interrupted or otherwise disturbed while the prosthetic valve is being located.

Further, placement of anchor stent 210/310 does not involve disturbance of the native valve leaflets 414. Accordingly, native valve leaflets 414 may continue to function while anchor stent 210/310 is being delivered and deployed. Therefore, functioning of the native valve leaflets 414 is only interrupted during placement of the valve component 240, which is simplified due to connection to anchor stent 210/310 rather than precise engagement with portions of the anatomy.

Optionally, the anchor stent could be made with a higher radial force but shorter length, which would still allow it to more easily navigate tortuous anatomy.

Further, because the stent frame of the valve can be made to have less radial force, it would be easier to design a sheath that would allow for recapturing the valve.

Although some examples of advantages have been described above, these are non-limiting in that other advantages of the modular valve prostheses 200/300 would be apparent to those skilled in the art.

It will also be understood that each feature of each embodiment discussed herein, and of each reference cited herein, can be used in combination with the features of any other embodiment. All patents and publications discussed herein are incorporated by reference herein in their entirety.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment

What is claimed is:

1. A modular valve prosthesis including a delivery configuration and a deployed configuration, the modular valve prosthesis comprising:
   an anchor stent including a self-expanding tubular frame member configured to be deployed against walls of the ascending aorta and attachment members extending inwardly from an internal surface of the tubular frame member; and
   a valve component separate from the anchor stent in the delivery configuration, the valve component including a valve frame including a distal portion and a proximal portion, wherein in the deployed configuration the distal portion of the valve frame is deployed within the tubular frame member such that the distal portion of the valve frame engages with the attachment members of the tubular frame member, and a prosthetic valve coupled to the proximal portion of the valve frame, wherein in the deployed configuration, the proximal portion of the valve frame is disposed proximal of the anchor stent such that the prosthetic valve is proximal of a proximal end of the anchor stent.

2. The modular valve prosthesis of claim 1, wherein the valve frame comprises a self-expanding stent with a plurality of cells.

3. The modular valve prosthesis of claim 2, wherein the attachment members of the tubular frame member comprise a plurality of rows of barbs and wherein the barbs are configured to couple with the cells of the distal portion of the valve frame in the deployed configuration.

4. The modular valve prosthesis of claim 1, wherein the valve component includes a valve arm component extending radially outward and proximally away from the valve frame and configured engage the sinuses of the aortic valve in the deployed configuration.

5. The modular valve prosthesis of claim 4, wherein the valve arm component comprises a plurality of arms and each arm comprises a wire loop with a first end of the wire coupled to the valve frame, the wire extending proximally from the first end and bending back distally to a second end of the wire coupled to the valve frame spaced from the first end.

6. The modular valve prosthesis of claim 1, further comprising a proximal arm component attached to and extending in a proximal direction from the proximal end of the tubular frame member, wherein in the deployed configuration the proximal arm component is deployed in the sinuses of the aortic valve.

7. The modular valve prosthesis of claim 6, further comprising a distal arm component extending in a distal direction from a distal end of the tubular frame member and configured to be deployed in the brachiocephalic artery.

8. The modular valve prosthesis of claim 6, wherein the proximal arm component comprises three proximal arms with each proximal arm configured to be deployed in one of the three aortic sinuses.

9. The modular valve prosthesis of claim 6, wherein the proximal arm component comprises a plurality of proximal arms and each proximal arm comprises a wire loop with a first end of the wire coupled to the proximal end of the tubular frame member, the wire extending proximally from the first end and bending back distally to a second end of the wire coupled to the proximal end of the tubular frame member spaced from the first end.

10. The modular valve prosthesis of claim 9, wherein the proximal arms comprise three proximal arms with each proximal arm configured to be deployed in one of the three aortic sinuses.

* * * * *